United States Patent [19]

Garcia

[11] 4,081,909
[45] Apr. 4, 1978

[54] ORTHODONTIC PLIERS

[76] Inventor: Francisco G. Garcia, Box A B, Rio Piedras, P.R. 00928

[21] Appl. No.: 710,125

[22] Filed: Jul. 30, 1976

[51] Int. Cl.² ............................................. A61C 13/22
[52] U.S. Cl. ....................................................... 32/66
[58] Field of Search ............................. 32/66; 140/106

[56] References Cited

U.S. PATENT DOCUMENTS

| 74,601 | 2/1868 | Rothschild | 140/106 |
| 3,626,995 | 12/1971 | Keenan | 140/106 |

*Primary Examiner*—Robert Peshock
*Attorney, Agent, or Firm*—Berman, Aisenberg & Platt

[57] ABSTRACT

An orthodontic pliers especially useful for bending the alignment wire end during all phases of the Begg orthodontic technique. The pliers comprise a pair of pivoted jaw members from the ends of which integrally extend a male and female beak which are preferably formed at substantially right angles to their respective jaws. In a preferred embodiment, the male beak comprises a substantially cylindrical member that mates with the female beak which is comprised of a semi-tubular upstanding member having an inner arcuate surface to cooperate with the male member. The pliers enable quick and easy bending of the arch wire ends without deforming the main arch wire.

6 Claims, 9 Drawing Figures

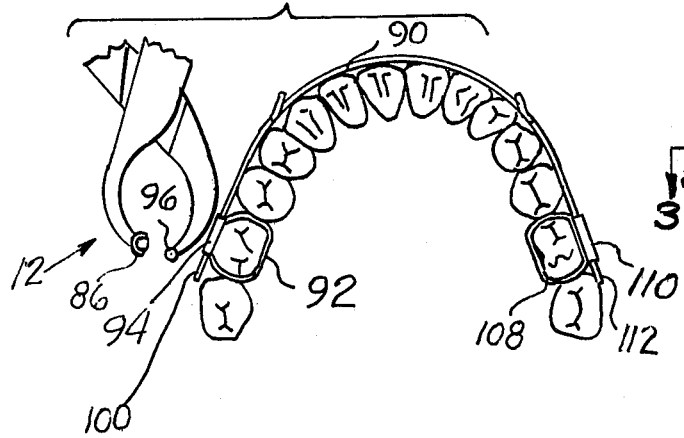
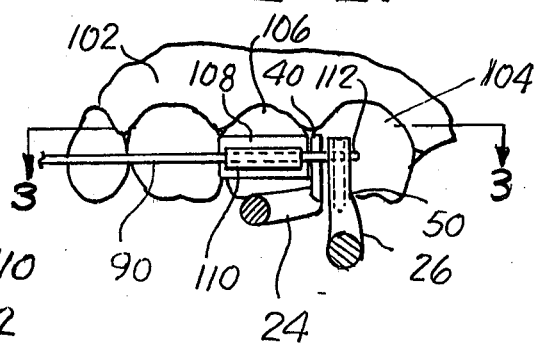
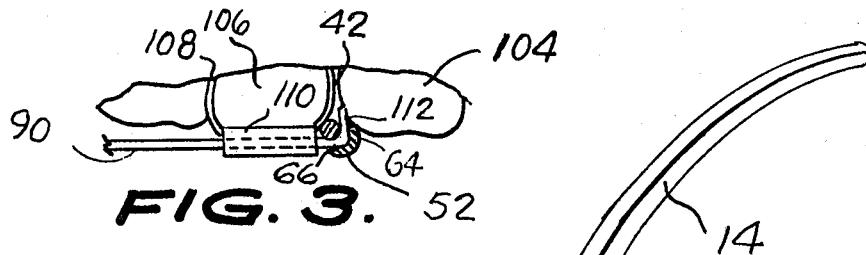
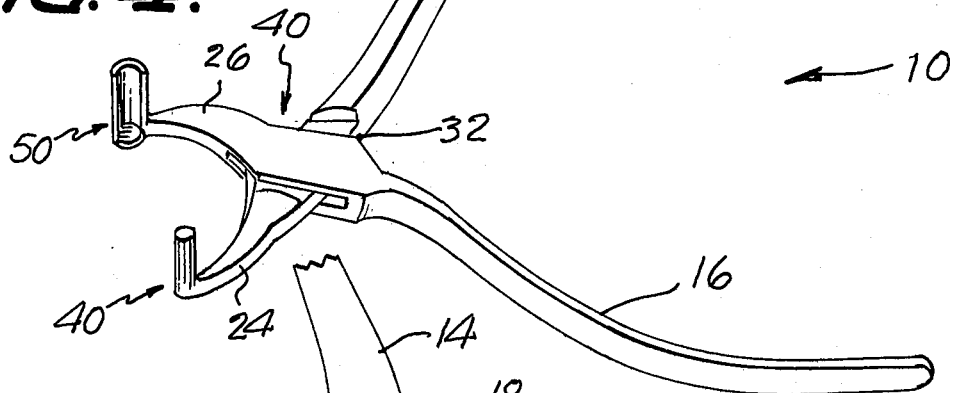
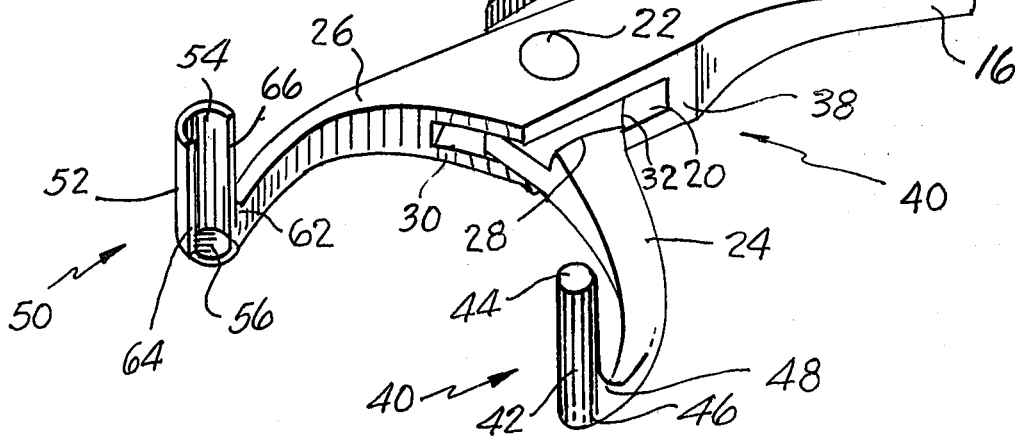

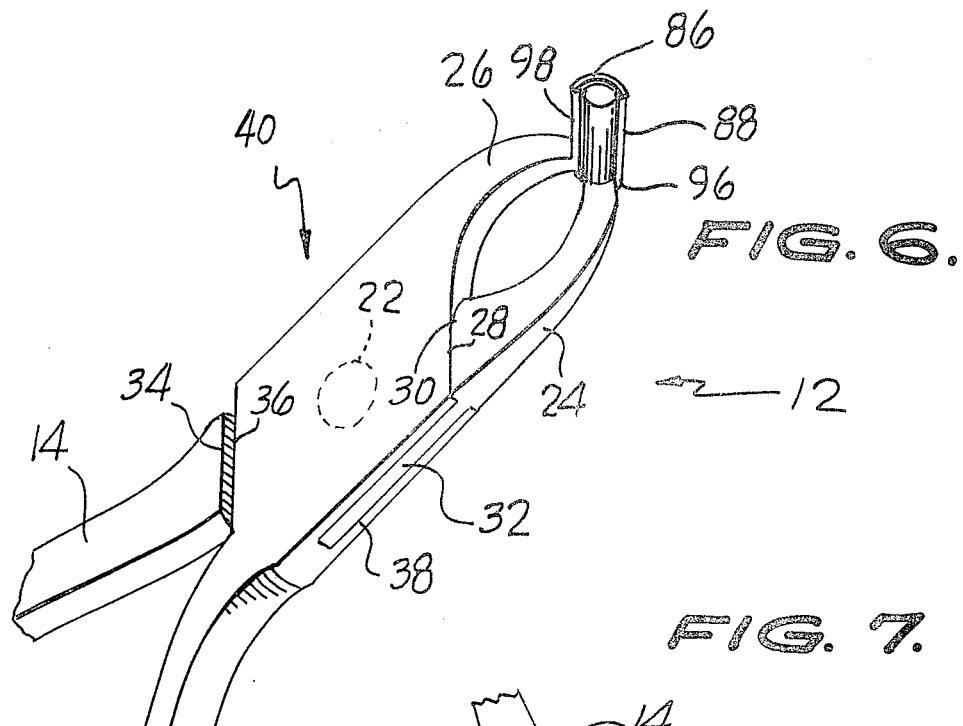

ORTHODONTIC PLIERS

BACKGROUND OF THE INVENTION

1. Field of the Invention

The present invention is related to orthodontic pliers and, more particularly, is directed to an orthodontic pliers for bending the distal end of round arch wires utilized during various techniques of orthodontic treatments.

2. Description of the Prior Art

Round arch wires are utilized in many different orthodontic treatment techniques. One of the most prevalant of these is known as the Begg technique which is accomplished in three phases, each of which requires the bending of the distal end of the arch wire as continuous adjustments are effectuated.

Many orthodontic pliers are presently available, but none, to the best of my knowledge, provide an easy, safe, and effective means for bending the arch alignment wire in a satisfactory manner. Utilization of presently available pliers frequently results in undesirable deformation or distortion of the main arch wire. Utilization of such improperly designed pliers can result in unfavorable tooth and arch movement.

Another serious drawback associated with the utilization of prior art pliers concerns patient discomfort. With presently available pliers, it is extremely difficult, if not impossible, to effectuate an inward bend of the distal end of the arch wire. In patients having small mouths, particularly, the end of the arch wire may be bent only upwardly or downwardly, which leaves the end of the wire adjacent the cheek and gum of the patient. This, in turn, can lead to scraped cheeks, gums, and the like, along with the concomitant discomfort and dissatisfaction on the part of the patient. Cut gums and a sore mouth are, quite obviously, detrimental to the necessary cooperation of the patient during orthodontic treatment. This is especially true during the early stages of treatment when utilization of such round arch wires are prevalent.

The arch wires are, in the Begg technique, positioned through buccal tubes positioned on the outside of tooth bands which are positioned about a posterior bicuspid. It is quite important to maintain the arch alignment wire completely straight within the buccal tube. Presently available orthodontic pliers make this requirement extremely difficult to attain.

Prior art United States patents of which I am aware which are illustrative of the state of the art include: U.S. Pat. Nos. 1,103,606; 1,108,493; 1,594,143; 2,725,632; 2,954,606; 3,146,804; 3,244,201; 3,727,316; 2,375,094; 3,774,306; and 3,804,132.

OBJECTS AND SUMMARY OF THE INVENTION

It is therefore a primary object of the present invention to provide an orthodontic pliers which overcomes all of the disadvantages noted above with respect to prior art pliers.

Another object of the present invention is to provide an orthodontic pliers which may be utilized in any orthodontic technique which requires the bending of round alignment wires and which accomplishes same in a simple, safe, and reliable fashion.

A further object of the present invention is to provide a novel and unique orthodontic pliers which may be easily utilized by the orthodontist in even the smallest mouths to achieve simple and accurate inward bending of the distal end of a round arch wire while preventing distortion of the remaining portion of the alignment wire to prevent unfavorable tooth and arch movement.

An additional object of the present invention is to provide a unique orthodontic pliers which may be utilized in all three phases of the Begg orthodontic technique for adjusting the wire ends without deforming the main arch wire.

A still further object of the present invention is to provide a simple, easy to manufacture, and highly desirable orthodontic pliers which greatly promotes patient comfort and enhances patient cooperation by alleviating a serious source of patient discomfort.

The foregoing and other objects are attained in accordance with one aspect of the present invention through the provision of an orthodontic pliers which comprises first and second pivotally coupled jaw members, and means integrally extending substantially perpendicularly from the respective ends of the jaw members for bending a wire placed therebetween in a direction substantially perpendicular to the bending means. In a preferred embodiment, the bending means comprises a substantially cylindrical member formed on the first jaw member and a semi-tubular member formed on the second jaw member for mating engagement with the cylindrical member. The mating surfaces of the bending means may be tapered.

In accordance with other aspects of the present invention, an orthodontic pliers are provided which comprises first and second jaw members pivotally coupled to each other for relative movement within first and second planes that are defined by the outermost surfaces of the jaw members. The pliers include first and second wire bending means connected to the first and second jaw members, respectively, and which extend substantially transversely from at least the first plane. The first and second wire bending means are comprised of mating surfaces which cooperate to bend a wire placed therebetween in a direction parallel to the first plane, preferably inwardly between adjacent teeth. More particularly, the first wire bending means comprises a male member having an arcuate outer surface and integrally extending substantially transversely from the first jaw member, while the second wire bending means comprises a female member having an arcuate inner surface for mating with the male member and which integrally extends substantially transversely from the second jaw member. In one embodiment, the arcuate surfaces of the male and female members are substantially cylindrical, while in an alternative embodiment, the arcuate surfaces may be substantially conical or tapered.

In an alternative structure and in accordance with yet other aspects of the present invention, the first and second wire bending means extend substantially transversely from both said first and second planes of said first and second jaw elements. In this embodiment, the first and second wire bending means respectively comprise a male member having an arcuate outer surface and a female member having an arcuate inner surface, the male and female members preferably extending integrally and substantially transversely from their respective jaw members. The male member extends above and below the end of the first jaw member, while female member extends similarly both above and below the end of the second jaw member. The male and female members of each of the jaw members are preferably unitary in construction. Utilization of this embodiment obviates the need for a separate set of complementary pliers in that it allows bending of the arch wire ends of both the upper and lower, left and right arch wires with a single instrument.

BRIEF DESCRIPTION OF THE DRAWINGS

Various objects, features and attendant advantages of the present invention will be more fully appreciated as the same become better understood from the following detailed description thereof when considered in connection with the accompanying drawings, in which:

FIG. 1 is a plan view of a human dental arch which is helpful in understanding one technique for which the preferred embodiment of the present invention is useful;

FIG. 2 is an enlarged side view of a portion of the human dental arch of FIG. 1 which illustrates one step in the utilization of the orthodontic pliers of the present invention;

FIG. 3 is a further diagrammatic representation taken along line 3—3 of FIG. 2 which illustrates a second step in the utilization of the preferred embodiment orthodontic pliers of the present invention;

FIG. 4 is a perspective view illustrating a preferred embodiment of the orthodontic pliers of the present invention in an open position;

FIG. 5 is an enlarged perspective view of the preferred embodiment of FIG. 4 which illustrates the structure of the pliers in greater detail;

FIG. 6 is a perspective view of a companion pliers of the embodiment illustrated in FIGS. 4 and 5, in a closed condition;

FIG. 7 is a perspective view of an alternative embodiment of the orthodontic pliers in accordance with the present invention;

FIG. 8 is a sectional view of the mating members in a closed condition of the alternative embodiment illustrated in FIG. 7; and FIG. 9 is a perspective view illustrating yet another alternative construction of the wire bending members in accordance with the teachings of the present invention.

DETAILED DESCRIPTION OF THE PREFERRED EMBODIMENTS

Referring now to the drawings, wherein like reference numerals represent identical or corresponding parts throughout the several views, and more particularly to FIG. 4 thereof, a preferred embodiment of the orthodontic pliers according to the present invention is indicated generally by the reference numeral 10.

Orthodontic pliers 10 are designed for bending round arch wires which is required, for example, during all three phases of the Begg orthodontic technique. The pliers 10 illustrated in FIGS. 4 and 5 require the utilization of a complementary companion pliers which is indicated generally by the reference numeral 12 in FIG. 6. As will become more clear hereinafter, pliers 10 illustrated in FIGS. 4 and 5 are utilized for bending the distal end of the arch wires at the left upper and right lower positions of the mouth, while its companion pliers 12 are utilized to bend the arch wires at the right upper and left lower mouth positions. Each of the pliers 10 and 12 embody the same structural concepts, and are identical but for their left-right symmetry, as will be appreciated by a person of ordinary skill in this art.

Referring more particularly to FIGS. 4 and 5, pliers 10 includes a pair of standard design handles 14 and 16 which cross in a pivoted shank portion 40. Shank portion 40 is comprised of a reduced thickness portion 18 of handle 14 which fits through a slotted aperture 20 extending from handle 16.

A jaw portion 24 extends from the reduced thickness portion 18 of handle 14, while a jaw portion 26 extends as the operating end of handle 16. As is conventional, handle 14, reduced portion 18, and jaw portion 24 are integrally cast, as are handle 16 and jaw 26. A pivot pin 22 is positioned through the shank portion 40 in a conventional fashion in order to permit pivotal rotation of the jaw members 24 and 26 which may be thought of as occurring within a pair of parallel planes defined by the outer surfaces of the jaw members.

Jaw 24 includes vertical surface 28 which mates with an arcuate surface 30 formed on jaw 26, while handle 14 includes surface 34 that mates with a complementary surface 36 formed in handle 16. Similarly, the reduced thickness pivot portion 18 includes a surface 32 which aligns with the outer surface 38 of the slotted shank 40, the closed position of the pliers being more evident from FIG. 6.

Positioned at the end of jaw portion 24 and extending transversely therefrom is a first bending member in the form of a male beak which is indicated generally by the reference numeral 40. Similarly, extending transversely from the end of jaw portion 26 is a second bending member in the form of a female beak indicated generally by the reference numeral 50.

The male beak or bending member 40 in a preferred embodiment comprises a substantially cylindrical body 42 which is integrally formed and extends upwardly from the end 46 of jaw 24. Beak 40 includes a flat round top portion 44 and preferably has excess material 48 included at the junction of its base and the end 46 of jaw 24 to provide sufficient strength against fracture.

Female beak 50 includes a substantially semi-cylindrical shell or tubular member 52 which is designed to mate with the substantially cylindrical male member 42 in a manner to become more clear hereinafter. The semi-cylindrical shell 52 is formed on the tip of jaw member 26 at an oblique angle with respect to the longitudinal axis of the pliers 10, as more particularly evidenced in FIGS. 3 and 6. The oblique angle placement of shell 52 on jaw 26 assists in the bending operation in a manner to become more clear hereinafter.

The female beak 50 further includes an inner concave mating surface 54, a base 56, and an integrally formed step of strut support 62 for providing additional strength at the junction with the tip of jaw 26. The semi-cylindrical or tubular shell 52 may be further defined by a leading edge 64 and a trailing edge 66.

Referring now to FIG. 6, the complementary pliers 12 is illustrated and the same reference numerals are provided but for the wire bending members 40 and 50. In FIG. 6, reference numeral 96 refers to the male beak, while reference numeral 86 indicates the cooperating female beak having a leading edge 88 and a trailing edge 98. FIG. 6 in showing the pliers 12 in a closed or clamped condition illustrate more clearly the oblique placement of female beak 86 with respect to the longitudinal axis of pliers 12.

Referring now to FIGS. 1 through 3, utilization of the orthodontic pliers of the present invention just described in connection with FIGS. 4 through 6 will now be described. FIG. 1 is a plan view of a human dental arch which illustrates the well known placement of a round arch wire 90 through a pair of buccal tubes 94 and 110 which are respectively formed on the outer periphery of a pair of tooth bands 92 and 108. Tooth bands 92 and 108 are positioned in the well known fashion about posterior bicuspids.

Reference numerals 100 and 112 respectively indicate the distal ends of arch wire 90 in their normal, unbent state. With orthodontic pliers previously available, the distal ends 100 and 112 of arch wire 90 could only be bent upwardly or downwardly, resulting in positions substantially perpendicular to the plane of the FIG. 1 drawing.

However, by virtue of the present invention, the arch wire ends 100 and 112 may be easily and safely bent inwardly at a substantially 90° angle between adjacent teeth in a fashion to be described.

FIG. 1 illustrates the complementary pliers 12 having bending means 96 and 86 in position just prior to application thereof to bend arch wire end 100.

FIG. 2 is an enlarged side view of the arch wire 90 shown positioned through the buccal tube 110 which is, in turn, mounted on tooth band 108 wrapped around bicuspid 106. In bending arch wire end 112 of wire 90, the pliers 10 illustrated in FIGS. 4 and 5 are preferably utilized. FIG. 2 illustrates the initial insertion of male beak 40 behind the end of arch wire 112 adjacent the point at which a bend is desired. Jaw 26 is then pivoted towards substantially stationary jaw 24, and leading edge 64 engages the wire end 112 for force same about the pivot created by cylindrical male beak 42 to achieve the bend illustrated in FIG. 3.

It is seen from FIG. 3 that the arch wire end 112 is easily and simply positioned between adjacent teeth 104 and 106 in a fashion which cannot injure either the gum or the cheek of the patient. The oblique setting of semi-tubular member 52 can now be fully appreciated as it allows frontal insertion of the pliers 10 and bending of the arch wire end 112 without undue manipulation. It can also be appreciated that the bending of the arch wire end 112 can be accomplished without distorting the portion of the arch wire 90 within buccal tube 110.

Referring now to FIGS. 7 and 8, an alternative embodiment of the present invention is illustrated by means of which the complementary pair of pliers 10 and 12 illustrated in FIGS. 4 through 6 have been combined into a single instrument indicated generally by the reference numeral 120. Pliers 120 are constructed substantially the same as the above-described pliers, with the exception of the combination beaks 70 and 80 formed at the ends of jaw members 24 and 26. Beak 70 comprises an upper cylindrical male member 72 juxtaposed and substantially coaxial with a lower cylindrical male member 74. Members 72 and 74 are preferably integrally formed, and are connected to the end of jaw member 24 at their approximate midpoint 75.

Beak 80 comprises an upper cylindrical female member 82 juxtaposed and substantially coaxial with a lower cylindrical female member 84. Female members 82 and 84 are preferably integrally formed and are connected to the end of jaw member 26 at their approximate midpoint 85.

As indicated in FIG. 8, female member 82 mates in a working relationship with male member 72, while female member 84 mates in a working relationship with male member 74. As will be apparent from a comparison of the pliers 120 with the pliers 10 and 12, bending members 72 and 82 are equivalent to the pliers 10 and enable bending of the left upper and right lower arch wire ends, while bending members 74 and 84 are equivalent to the pliers 12 which enable bending of the right upper and left lower arch wire ends. By virtue of the combination embodiment pliers 120, only a single pair of pliers need be utilized by the practitioner for the bending of all arch wire ends, although it is conceivable that in some instances separate pliers 10 and 12 may be preferable.

Referring now to FIG. 9, an alternative construction to the bending members 40 and 50 of the pliers 10 illustrated in FIGS. 4 and 5 is shown. In this modification, the bending members comprise a female beak 114 and a male beak 116 each of which include slightly tapered outer surfaces which are somewhat conically shaped. This embodiment enables greater structural integrity of the bending members at their base portions 118 and 120 which define the junctions with the ends of the jaw members 26 and 24, respectively. As exemplary of the taper which may be provided to bending members 114 and 116, their uppermost or tip portions may be made 0.045 inch in diameter, tapering outwardly and downwardly to a base having a 0.055 inch diameter, although other dimensions may be equally acceptable.

As further examples of dimensions which may be utilized in the construction of the pliers of my invention, their overall length including the handle portions may be on the order of 5.25 inches, the height of the unidirectional beak of the FIGS. 4 through 6 embodiments may be on the order of 0.25 inch, the height of the beaks of the pliers 120 may each be on the order of 0.50 inch, and the inner diameter of the semi-tubular beak 50 may be 0.055 inch which would be equal to the outer diameter of the cylindrical member 40. Finally, the width of the shank 40 could be on the order of 7/16 inch.

Obviously, numerous modifications and variations of the present invention are possible in light of the above teachings. It is therefore to be understood that within the scope of the appended claims the invention may be practiced otherwise than as specifically described herein.

I claim as my invention:

1. An orthodontic pliers, which comprises:
   first and second jaw members pivotally coupled to each other and having handle means extending laterally from one end thereof and wire bending means extending transversely from the other end thereof;
   said wire bending means including a first elongated bending member having an arcuate outer surface and connected to said other end of said first jaw member at a first junction point, and a second elongated bending member connected to said other end of said second jaw member at a second junction point and comprising a semi-tubular body having an arcuate inner surface complementary to and adapted to mate with said arcuate outer surface of said first elongated bending member;
   the major portion of said first and second elongated bending members extending substantially beyond their respective junction points with said first and second jaw members for permitting intra-oral bending of orthodontic arch wires therebetween.

2. The orthodontic pliers as set forth in claim 1, wherein said first and second elongated bending members extend only unidirectionally from said first and second junction points, respectively.

3. The orthodontic pliers as set forth in claim 1, wherein said first and second elongated bending members extend bi-directionally from said first and second junction points, respectively.

4. The orthodontic pliers as set forth in claim 1, wherein said wire bending means are comprised of mating surfaces which cooperate to bend a wire placed therebetween in a plane substantially parallel to the plane of movement of said jaw members.

5. The orthodontic pliers as set forth in claim 1, wherein said arcuate surfaces of said first and second bending members are substantially cylindrical.

6. The orthodontic pliers as set forth in claim 1, wherein said arcuate surfaces of said first and second bending members are substantially conical.

* * * * *